United States Patent
Lenhart et al.

(10) Patent No.: US 6,486,375 B1
(45) Date of Patent: Nov. 26, 2002

(54) PROCESS FOR RECOVERING HYDROCARBONS FROM INERT GAS-HYDROCARBON VAPOR MIXTURES

(75) Inventors: Melissa G. Lenhart, Haskell, OK (US); Harold L. Dinsmore, Tulsa, OK (US); Scott J. Fox, Broken Arrow, OK (US)

(73) Assignee: John Zink Company, LLC, Tulsa, OK (US)

( * ) Notice: Subject to any disclaimer, the term of this patent is extended or adjusted under 35 U.S.C. 154(b) by 0 days.

(21) Appl. No.: 09/847,486

(22) Filed: May 2, 2001

(51) Int. Cl.[7] ................................................ C07C 7/12
(52) U.S. Cl. ...................... 585/820; 585/821; 585/822; 585/826
(58) Field of Search ................................ 585/820, 821, 585/822, 826

(56) References Cited

U.S. PATENT DOCUMENTS

| | | | |
|---|---|---|---|
| 4,261,716 A | 4/1981 | Schwartz et al. | 55/387 |
| 4,276,058 A | 6/1981 | Dinsmore | 55/48 |
| 4,331,456 A | 5/1982 | Schwartz et al. | 55/26 |
| 4,338,101 A | 7/1982 | Tuttle | 55/48 |
| 4,343,629 A | 8/1982 | Dinsmore et al. | 55/28 |
| 5,154,735 A | 10/1992 | Dinsmore et al. | 55/25 |
| 5,345,771 A | 9/1994 | Dinsmore | 62/18 |
| 5,951,741 A | 9/1999 | Dahl et al. | 95/11 |
| 6,106,243 A | 8/2000 | Popov | 417/313 |
| 6,109,882 A | 8/2000 | Popov | 417/53 |
| 6,120,254 A | 9/2000 | Popov | 417/151 |
| 6,164,567 A | 12/2000 | Popov | 239/428.5 |

Primary Examiner—Marian C. Knode
Assistant Examiner—Tam M. Nguyen
(74) Attorney, Agent, or Firm—C. Clark Dougherty, Jr.

(57) ABSTRACT

An improved process for recovering hydrocarbons from an inlet inert gas-hydrocarbon vapor mixture is provided. The inlet mixture is caused to flow through a first bed of solid adsorbent whereby hydrocarbon vapors are adsorbed on the bed and a residue gas stream comprised of substantially hydrocarbon-free inert gas is produced. The hydrocarbon-free inert gas is vented and a second bed of solid adsorbent having hydrocarbon vapors adsorbed thereon is evacuated with an ejector operated by a motive liquid. A major portion of the hydrocarbon vapors is desorbed from the bed and an inert gas and hydrocarbon-rich vapor mixture commingled with the motive liquid is produced. The inert gas and hydrocarbon-rich vapor mixture is separated from the motive liquid and conducted to a point of additional processing or disposal. The flow pattern of the inlet inert gas-hydrocarbon vapor mixture is periodically changed whereby when the bed through which the inlet inert gas-hydrocarbon vapor mixture is flowing becomes loaded, the inlet inert gas-hydrocarbon vapor mixture is caused to flow through the bed which has just been evacuated and the bed loaded with adsorbed hydrocarbon vapors is caused to be regenerated.

30 Claims, 6 Drawing Sheets

PROCESS FOR RECOVERING HYDROCARBONS FROM INERT GAS-HYDROCARBON VAPOR MIXTURES

BACKGROUND OF THE INVENTION

1. Field of the Invention

The present invention relates to a process for recovering hydrocarbons from inert gas-hydrocarbon vapor mixtures, and more particularly, to an improved process for recovering vaporized gasoline, distillates, benzene, solvents and the like from a mixture thereof with inert gas.

2. Description of the Prior Art

In handling multi component and single component hydrocarbon liquids such as gasoline, inert gas hydrocarbon vapor mixtures are readily produced which cannot be vented directly to the atmosphere due to the resulting pollution and fire or explosion hazard. As a result, a variety of processes have heretofore been developed and used for removing hydrocarbon vapors from inert gas-hydrocarbon vapor mixtures whereby the remaining inert gas can be safely vented to the atmosphere. The removed hydrocarbon vapors are recovered, processed further or disposed of.

A particularly suitable prior art process for recovering hydrocarbons from air-hydrocarbon vapor mixtures and the like is described in U.S. Pat. No. 5,154,735 issued to Dinsmore et al. on Oct. 13, 1992. The process comprises the steps of flowing the inlet air-hydrocarbon vapor mixture through a first bed of solid adsorbent whereby hydrocarbons are adsorbed on the bed and a residue gas stream comprised of substantially hydrocarbon-free air which is vented to the atmosphere is produced. A second bed of solid adsorbent having hydrocarbons adsorbed thereon is regenerated by vacuum pumping whereby hydrocarbons are desorbed from the bed and a hydrocarbon rich air-hydrocarbon mixture is produced. A substantial portion of the hydrocarbons are recovered from the hydrocarbon rich air-hydrocarbon vapor mixture produced during the regeneration. The beds of adsorbent are periodically changed from adsorption to regeneration and vice versa so that the bed which has just become loaded with adsorbed hydrocarbons is regenerated, i.e., evacuated and stripped of hydrocarbons and the bed which has just been regenerated adsorbs hydrocarbons. The evacuation of the beds during regeneration is accomplished in the process of U.S. Pat. No. 5,154,735 by vacuum pumping with a liquid seal vacuum pump. In order to increase the evacuation, a positive displacement booster pump connected upstream and in series with the liquid seal vacuum pump is utilized in combination with the introduction of a relatively small quantity of hydrocarbon-free air into the bed being evacuated whereby additional hydrocarbons are stripped from the bed. The further, evacuation accomplished by the booster pump and air stripping results in the bed being regenerated to a low hydrocarbon content and in substantially hydrocarbon-free air being vented to the atmosphere.

While the above described process utilizing a positive displacement booster pump in series with a liquid seal vacuum pump has achieved great commercial success, the cost of the pumps, their maintenance and their operation are expensive. Thus, there are needs for improved processes capable of regenerating beds of solid adsorbent to a very low hydrocarbon content which are less costly to install, operate and maintain.

SUMMARY OF THE INVENTION

The present invention provides improved processes for recovering hydrocarbon vapors from intermittent or continuous inlet inert gas-hydrocarbon vapor mixtures which meet the needs described above and overcome the deficiencies of the prior art. The improved processes of the present invention are basically comprised of the following steps. An inlet inert gas-hydrocarbon vapor mixture is flowed through a first bed of solid adsorbent having an affinity for hydrocarbons whereby hydrocarbons are adsorbed on the bed and a residue gas stream comprised of substantially hydrocarbon-free inert gas is produced. The substantially hydrocarbon-free inert gas is vented to the atmosphere. A second bed of solid adsorbent having hydrocarbons adsorbed thereon is evacuated with a simple ejector which is operated by a continuous motive liquid stream whereby a major portion of the hydrocarbons are desorbed from the bed and an inert gas-hydrocarbon-rich vapor mixture commingled with motive liquid is produced. The inert gas-hydrocarbon-rich vapor mixture is separated from the motive liquid and is processed further or disposed of. The flow pattern of the inlet inert gas-hydrocarbon vapor mixture is periodically changed so that when the bed through which the inlet inert gas-hydrocarbon vapor mixture is flowing becomes loaded with adsorbed hydrocarbons, the inlet inert gas-hydrocarbon vapor mixture is caused to flow through the bed which has just been evacuated and the bed loaded with adsorbed hydrocarbons is regenerated. The basic processes also preferably include the step of introducing a quantity of hydrocarbon-free inert stripping gas into the bed being evacuated whereby additional hydrocarbons are stripped from the bed and additional inert gas-hydrocarbon-rich vapor mixture co-mingled with motive liquid is produced.

In alternate embodiments of the basic process of the present invention, the motive liquid can be recirculated through the ejector or the motive liquid can be a continuous stream which passes through the ejector only once. In addition, the motive liquid can be a liquid which has an affinity for the desorbed hydrocarbon vapor whereby a major portion of the hydrocarbon vapor is absorbed in the motive liquid as it passes through the ejector.

In addition to the above described basic processes, the present invention provides a variety of additional process steps which can be utilized in accordance with this invention to liquefy and recover the desorbed hydrocarbon vapor.

It is, therefore, a general object of the present invention to provide improved processes for recovering hydrocarbons from inert gas-hydrocarbon vapor mixtures.

Other and further objects, features and advantages of the present invention will be readily apparent to those skilled in the art upon a reading of the description of preferred embodiments which follows when taken in conjunction with the accompanying drawings.

BRIEF DESCRIPTION OF THE DRAWINGS

FIG. 8 is a schematic illustration of apparatus for carrying out an alternate form of the additional process steps of FIG. 7 for liquefying and recovering the hydrocarbon vapor produced by a basic process.

FIG. 9 is a schematic illustration of apparatus for carrying out yet other additional process steps for liquefying and recovering the hydrocarbon vapor produced by a basic process.

DESCRIPTION OF PREFERRED EMBODIMENTS

Figure 1:
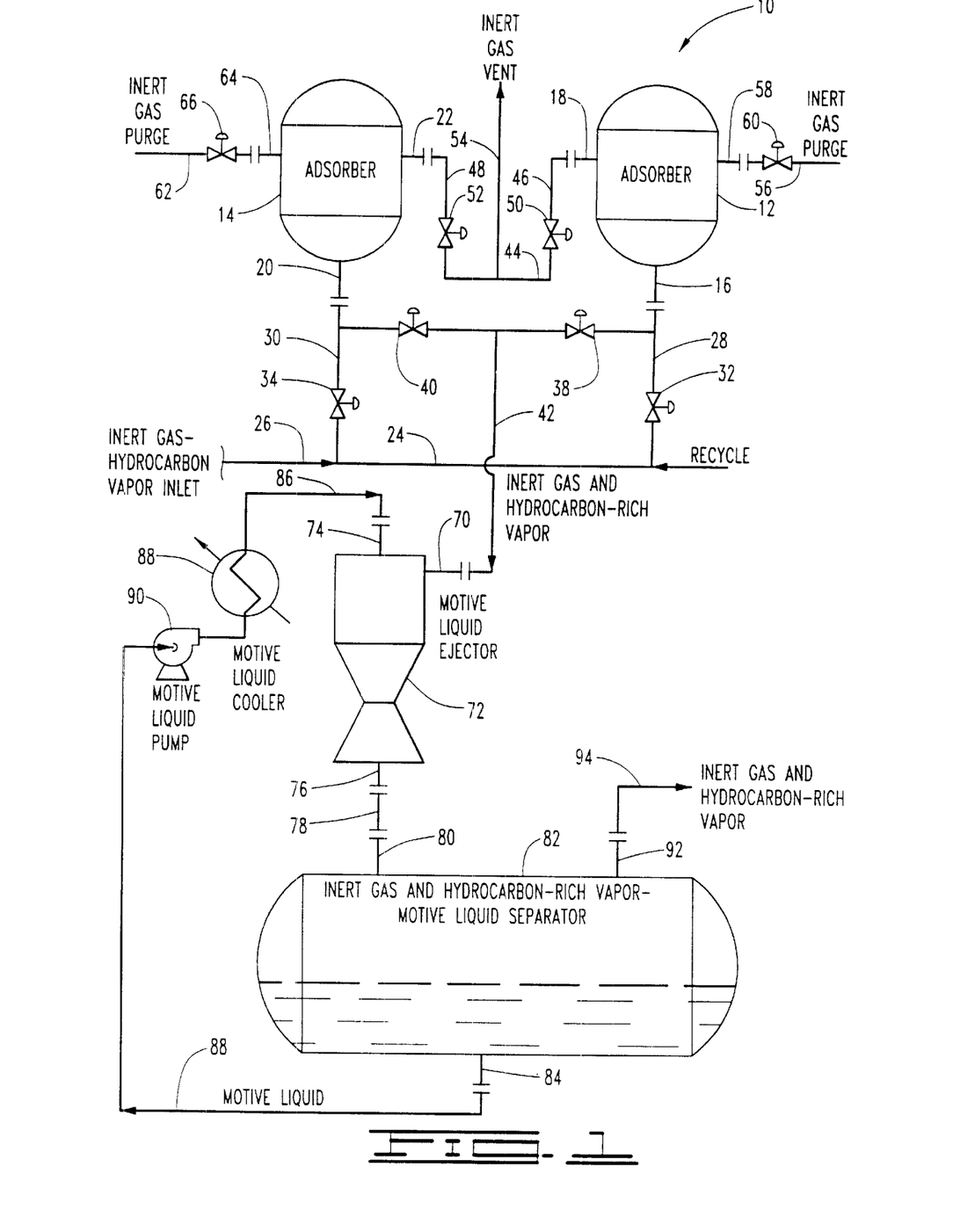
FIG. 1 is a schematic illustration of apparatus for carrying out a basic process of this invention.

Referring now to FIG. 1, apparatus for carrying out a basic process of the present invention is illustrated and generally designated by the numeral 10. The apparatus 10 is comprised of a pair of absorbers 12 and 14, each of which contains a bed of solid adsorbent through which gases can flow. Each of the adsorbers 12 and 14 are closed vessels and include connections on opposite sides of the beds of adsorbent contained therein, i.e., the adsorber 12 includes inlet and outlet connections 16 and 18 and the adsorber 14 includes inlet and outlet connections 20 and 22. While various solid adsorbents having an infinity for hydrocarbons can be utilized in the adsorbers 12 and 14, activated carbon is preferred in that it is particularly suitable for adsorbing light hydrocarbon vapors of the type found in inert gas-hydrocarbon vapor mixtures and for vacuum regeneration.

An inert gas-hydrocarbon vapor mixture inlet header 24 is provided connected to a conduit 26 which conducts an inlet mixture of inert gas and hydrocarbon vapor from a source thereof to the apparatus 10. The inert gas can be, but is not limited to, air, nitrogen, carbon dioxide and the like. The hydrocarbon vapor can be, but is not limited to, gasoline light end vapors, distillate light end vapors, benzene vapor, chlorinated and other hydrocarbon solvent light end vapors and alcohol vapors.

A pair of conduits 28 and 30 are connected to the header 24 and to the connections 16 and 20 of the adsorbers 12 and 14, respectively. Conventional switching valves 32 and 34, or their equivalents, are disposed in the conduits 28 and 30, respectively. A header 36 is connected to the conduits 28 and 30 at points thereon between the switching valves 32 and 34 and the connections 16 and 20 of the adsorbers 12 and 14. A pair of switching valves 38 and 40, or their equivalents, are disposed in the header 36 and a conduit 42 is connected to the header 36 at a point between the switching valves 38 and 40.

A residue gas header 44 is provided, and a pair of conduits 46 and 48 are connected to the header 44 and to the connections 18 and 22 of the adsorbers 12 and 14. Switching valves 50 and 52, or their equivalents, are disposed in the conduits 46 and 48, respectively, and a conduit 54 is connected to the header 44 for venting substantially hydrocarbon free residue inert gas to the atmosphere.

A conduit 56 connected to a source of stripping inert gas (not shown), which can optionally be heated, is connected to a inert stripping gas connection 58 in the adsorber 12. A switching valve 60, or the equivalent, is disposed in the conduit 56. In a like manner, stripping inert gas is conducted to the adsorber 14 by a conduit 62 connected to a connection 64 in the adsorber 14. A switching valve 66, or the equivalent, is disposed in the conduit 62.

The conduit 42 connected to the header 36 is connected to the suction connection 70 of a motive liquid ejector 72. The ejector 72 includes a motive liquid inlet connection 74 and an inert gas-hydrocarbon-rich vapor mixture-motive liquid outlet connection 76 which is in turn connected by a conduit 78 to an inlet connection 80 of an inert gas-hydrocarbon-rich vapor mixture-motive liquid separator 82. The separated motive liquid accumulates in the bottom of the separator 82 and is withdrawn therefrom by way of a connection 84. A conduit 86 connected to the connection 84 conducts the motive liquid withdrawn from the separator 82 to the motive liquid inlet connection 74 of the ejector 72. A motive liquid cooler 88, which can be a shell and tube heat exchanger, an air cooler, an evaporative cooler or the like, is disposed in the conduit 86 as is a motive liquid pump 90. The inert gas and hydrocarbon-rich vapor separated in the separator 82 is withdrawn therefrom by way of an outlet connection 92 and a conduit 94 connected thereto.

The motive liquid ejector 72 is operated by the motive liquid which is pumped into the ejector by the pump 90 by way of the connection 74. The high velocity flow of the motive liquid passing through the ejector 72 withdraws inert gas and hydrocarbon vapors from the adsorber 12 or 14 being regenerated thereby evacuating the adsorber. The motive liquid can be any suitable liquid including, but not limited to, glycol, water, petroleum based oils, hydrocarbon liquids, alcohols and various synthetic liquids. The motive liquid is continuously circulated from the separator 82, through the motive liquid cooler 88 and into the ejector 72 by the motive liquid pump 90.

The flow pattern of the inlet inert gas-hydrocarbon vapor mixture is periodically changed as is the bed of solid adsorbent being evacuated. That is, when the adsorbent bed through which the inlet inert gas-hydrocarbon vapor mixture is flowing becomes loaded with adsorbed hydrocarbons, the inlet inert gas-hydrocarbon vapor mixture is caused to flow through the bed which has just been evacuated and the bed loaded with adsorbed hydrocarbons is regenerated.

The ejector 72 functions as a jet pump to evacuate the adsorber being regenerated. A particularly suitable ejector (also referred to as a gas and fluid jet apparatus) for use in accordance with the present invention is described in U.S. Pat. No. 6,164,567 issued to Popov on Dec. 26, 2000 which is incorporated herein by reference. The ejector of U.S. Pat. No. 6,164,567 has an increased capacity and creates a greater depth of vacuum than prior art ejectors making it particularly suitable for use in the processes of this invention. The size of the ejector and the flow rate of the motive liquid through the ejector determine its capacity to withdraw gases from the adsorbers 12 and 14 and create the required vacuum therein. Generally, a motive liquid flow rate in the range of from about 100 to about 1,000 gallons per minute is required for the processes of this invention.

The inert gas and hydrocarbon-rich vapor mixture separated in the separator 82 is conducted by the conduit 94 to a point of further processing or disposal. Various preferred additional process steps which can be utilized with a basic process of this invention for liquefying and recovering the hydrocarbon-rich vapors are described hereinbelow.

Figure 2:
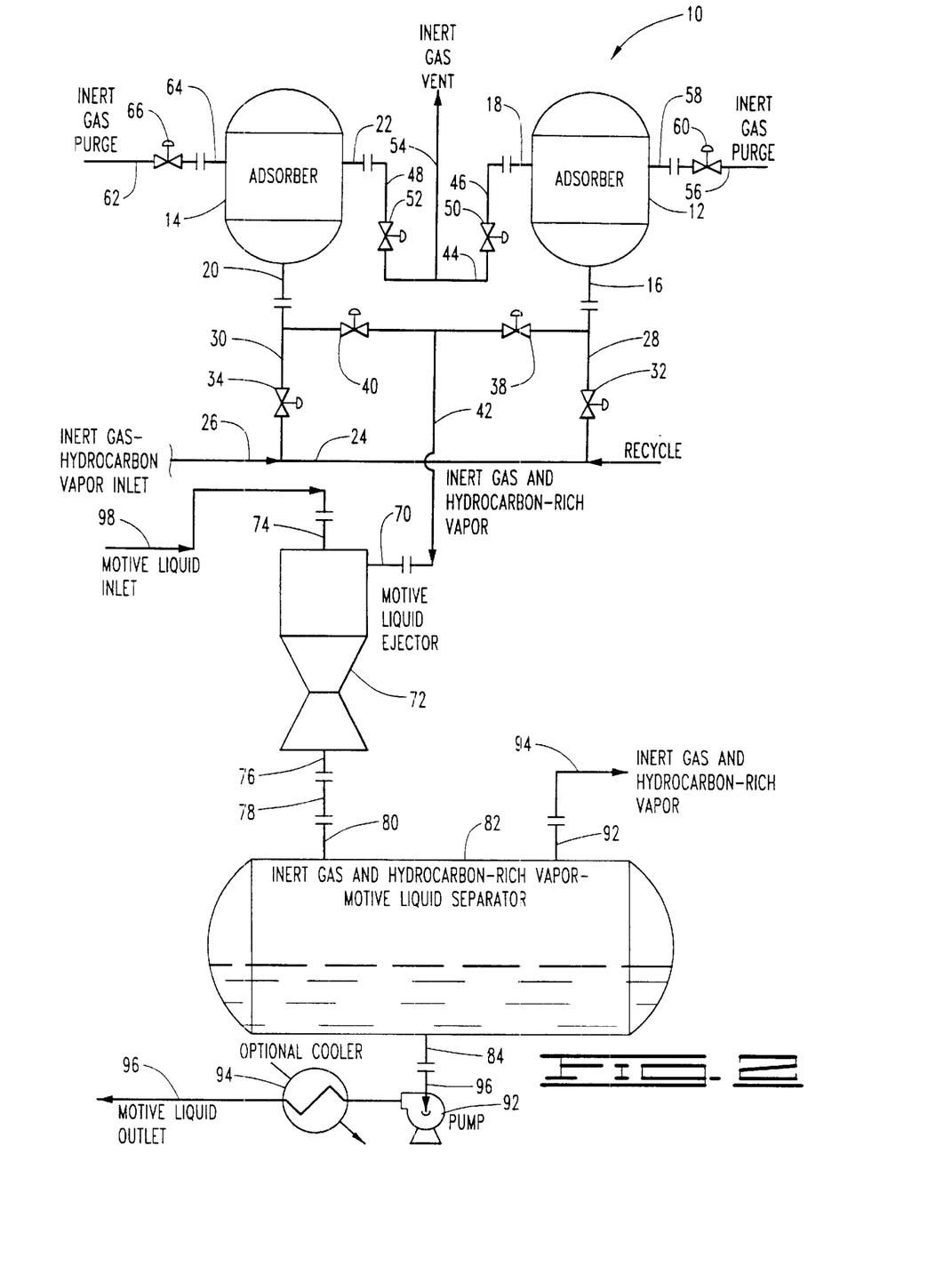
FIG. 2 is a schematic illustration of apparatus for carrying out another basic process of this invention.

Referring now to FIG. 2, the apparatus for carrying out a basic process of this invention utilizing a continuous stream of motive liquid which passes through the ejector only once is illustrated. The reference numerals of FIG. 2 are the same as those used in FIG. 1 except for the motive liquid inlet conduit 98, the motive liquid pump 92, the optional cooler 94 and the motive liquid outlet pump 96. That is, a continuous stream of motive liquid from a separate process or from storage (not shown) is utilized. The motive liquid enters the apparatus 10 by way of a conduit 98 which is connected to the motive liquid inlet connection 74 of the ejector 72. The motive liquid flows through the ejector 72 and separator 82 only once and is withdrawn from the separator by way of the outlet connection 84 and a conduit 96 having a pump 92 and an optional cooler 94 disposed therein. The conduit 96 and pump 92 return the stream of motive liquid to the separate process or storage facility.

Figure 3:
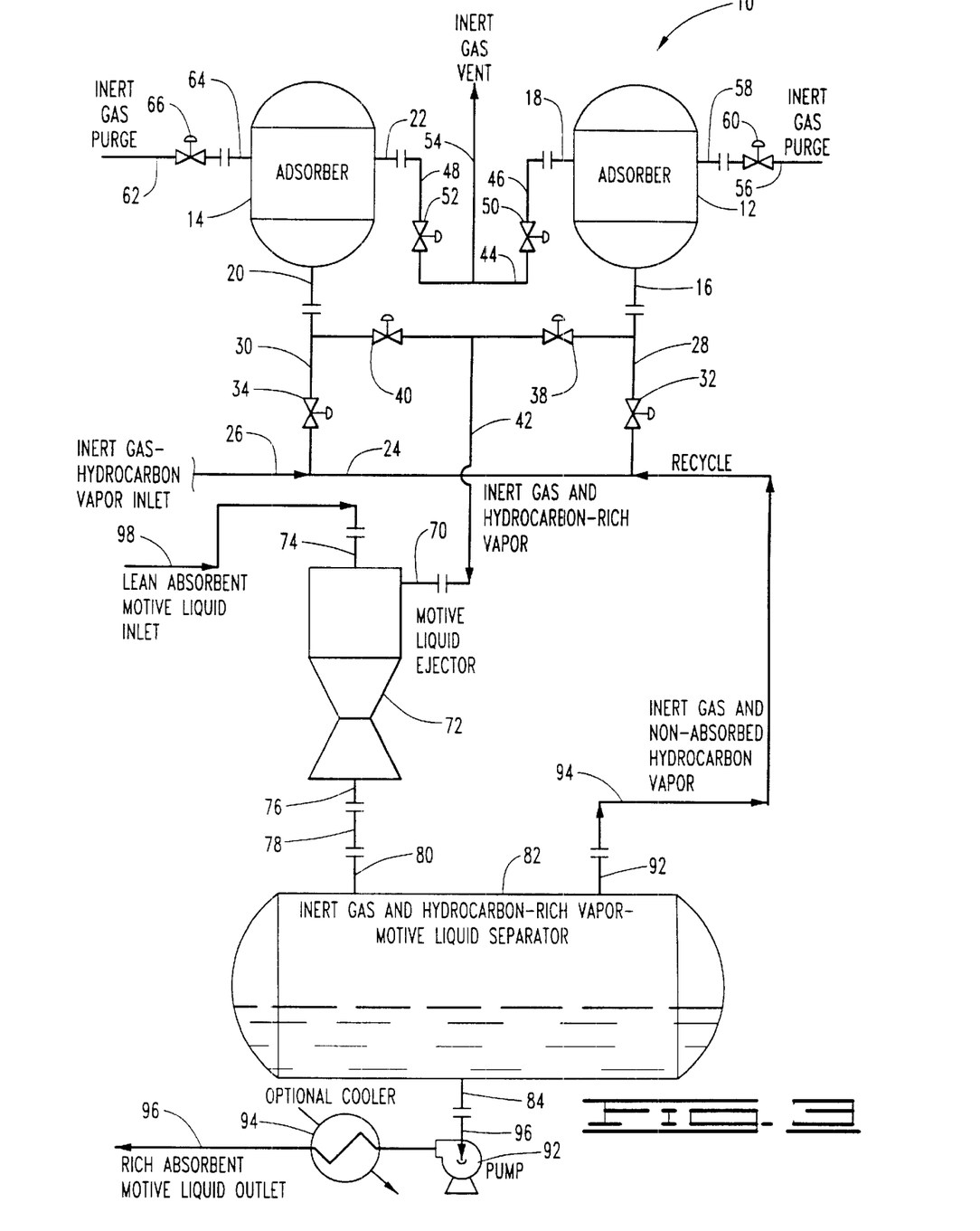
FIG. 3 is a schematic illustration of apparatus for carrying out still another basic process of the present invention.

Referring now to FIG. 3, the apparatus for carrying out another basic process of this invention is illustrated utilizing the same reference numerals as those used in FIG. 1. The only difference in FIG. 2 and FIG. 3 is that the motive liquid used has an affinity for hydrocarbon vapors (the motive liquid absorbs hydrocarbon vapors). That is, a continuous stream of a lean absorbent motive liquid from a separate process or storage facility is conducted by the conduit 98 to the inlet connection 74 of the ejector 72. Examples of lean absorbent motive liquids that can be used include, but are not limited to, gasoline, diesel oil, naphtha, kerosene and various hydrocarbon solvents and alcohols. The lean absorbent motive liquid flows through the ejector 72 wherein it causes inert gas and hydrocarbon-rich vapor to be withdrawn from the adsorber being regenerated into the ejector. As a result of the contact between the lean absorbent motive liquid and the inert gas and hydrocarbon-rich vapor within the ejector, a major portion of the hydrocarbon-rich vapor is absorbed therein. The resulting hydrocarbon-rich absorbent motive liquid is separated in the separator 82 and withdrawn therefrom by way of the connection 84 thereof, the conduit 96 and the pump 92. The pump 92 pumps the hydrocarbon-rich absorbent motive liquid through the conduit 96 and the optional cooler 94 and returns the hydrocarbon rich absorbent motive liquid to the separate process or storage. The inert gas and non-absorbed hydrocarbon vapor separated in the separator 82 is withdrawn therefrom by way of the connection 92 and conduit 94. The conduit 94 can be connected to the header 24 whereby the inert gas and non-absorbed hydrocarbon vapor is recycled to the adsorber 12 or 14 through which the inlet inert gas-hydrocarbon vapor mixture is flowing.

Figures 4, 5:
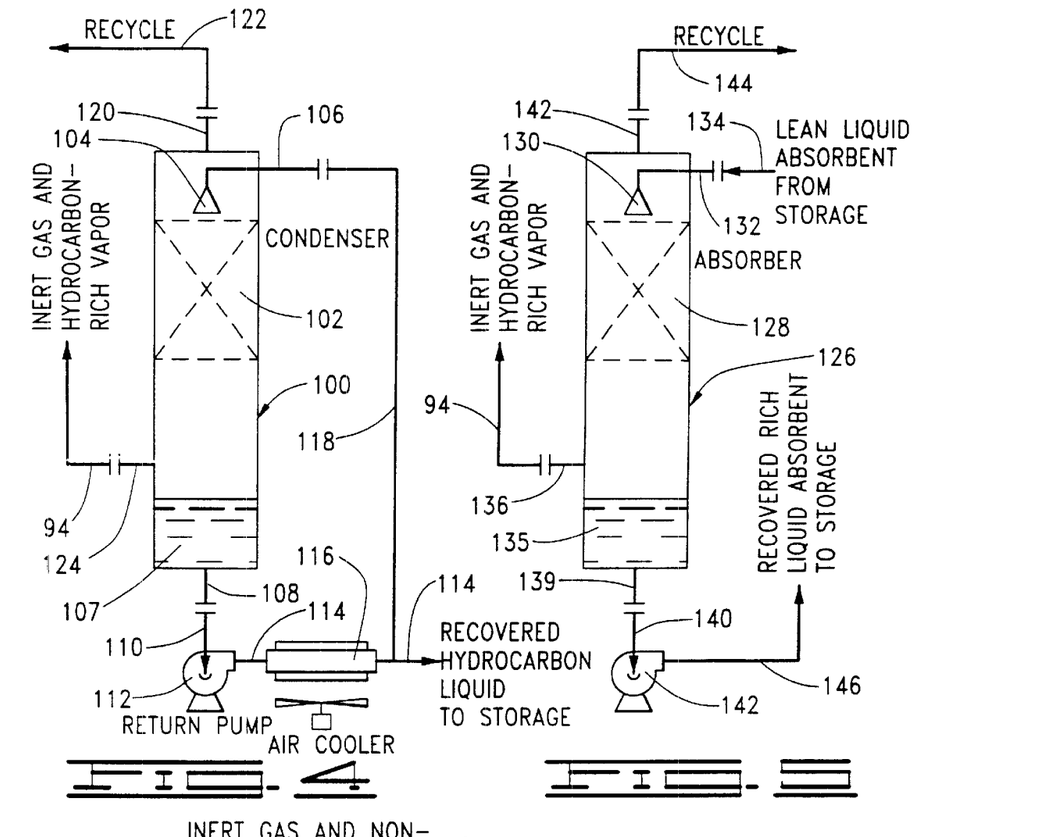
FIG. 4 is a schematic illustration of apparatus for carrying out additional process steps for liquefying and recovering the hydrocarbon vapors produced by a basic process of this invention.
FIG. 5 is a schematic illustration of apparatus for carrying out other additional process steps for liquefying and recovering the hydrocarbon vapors produced by a basic process of this invention.
Figure 5:
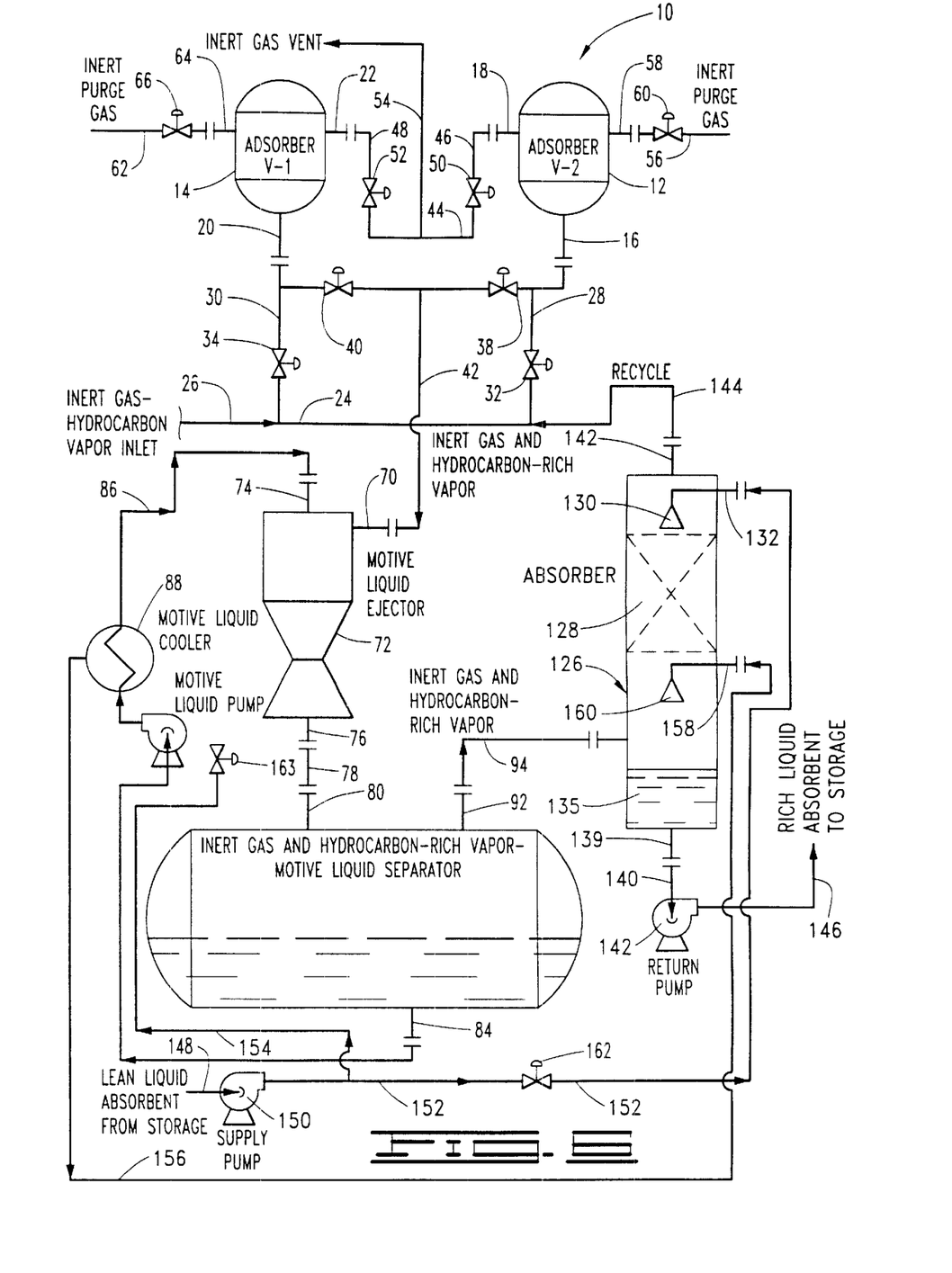

Referring now to FIG. 4, apparatus is illustrated for carrying out additional process steps that can be used for liquefying and recovering hydrocarbons from the inert gas and hydrocarbon-rich vapor stream produced by the basic processes described in connection with FIGS. 1 and 2. The apparatus is comprised of a condenser column 100 having a packed section or the equivalent 102, an internal spray nozzle 104 connected to an inlet connection 106, a condensed hydrocarbon liquid accumulator section 107, a condensed hydrocarbon liquid outlet connection 108, a non-condensed hydrocarbon and inert gases outlet connection 120 and an inert gas and hydrocarbon-rich vapor inlet connection 124. The conduit 94 from a basic process illustrated in FIG. 1 or FIG. 2 conducts inert gas and hydrocarbon-rich vapor to the condenser column 100. The inert gas and hydrocarbon-rich vapor flowing upwardly through the packed section 102 of the condenser column 100 is contacted by downwardly flowing condensed hydrocarbon liquid from the spray nozzle 104. The cool downwardly flowing condensed hydrocarbon liquid condenses a major portion of the hydrocarbon vapor in the upwardly flowing inert gas and hydrocarbon-rich vapor mixture. The resulting condensed hydrocarbons accumulate in the accumulator section 107 of the condenser column 100 and are withdrawn therefrom by way of the outlet connection 108. A conduit 110 leads the condensed hydrocarbons to a pump 112 which pumps the hydrocarbons into and through the conduit 114 connected thereto. A cooler 116 is disposed in the conduit 114. While the cooler 116 is illustrated as an air cooler, any suitable form of cooler can be utilized. A portion of the cooled hydrocarbons flowing through the conduit 114 is diverted into the conduit 118 with the remaining recovered hydrocarbons being conducted to storage. The side stream of hydrocarbons flowing through the conduit 118 passes by way of the connection 106 into and through the spray nozzle 104 and contacts the inert gas and hydrocarbon-rich vapor flowing upwardly as described above. The inert gas and the non-condensed hydrocarbon vapor remaining pass out of the column 100 by way of the connection 120 into the recycle conduit 122. The recycle conduit 122 returns the inert gas and non-condensed hydrocarbon vapor to the inlet header 24 of the basic process illustrated in FIGS. 1 or 2 whereby it flows into the adsorber through which the inlet inert gas-hydrocarbon vapor mixture is flowing.

Thus, the additional process steps for liquefying and recovering hydrocarbons from the inert gas and hydrocarbon vapor mixture produced by a basic process of this invention described in connection with FIG. 4 are comprised of: (1) contacting the inert gas and hydrocarbon vapor mixture with condensed hydrocarbon liquid whereby a major portion of the hydrocarbon vapor in the mixture is also condensed; (2) separating the condensed hydrocarbon liquid from the remaining inert gas and non-condensed hydrocarbon vapor; (3) recycling a portion of the separated condensed hydrocarbon liquid into contact with the inert gas and hydrocarbon vapor mixture in accordance with step (1); (4) conducting the remaining separated condensed hydrocarbon liquid to a point of further processing or storage, and (5) recycling the remaining inert gas and non-condensed hydrocarbon vapor to the inlet inert gas-hydrocarbon vapor mixture whereby the remaining inert gas and non-condensed hydrocarbon vapor flows into the bed of adsorbent wherein hydrocarbon vapors are being adsorbed.

Referring now to FIG. 5, an apparatus is shown for carrying out alternate additional process steps for liquefying and recovering hydrocarbons from the inert gas and hydrocarbon-rich vapor mixture produced by a basic process described in connection with FIGS. 1 or 2. The apparatus is comprised of an absorber column 126 having a packed section or the equivalent 128, an internal spray nozzle 130 connected to a lean liquid absorbent inlet connection 132, a rich liquid absorbent accumulator section 135, a rich liquid absorbent outlet connection 139, an inert gas and hydrocarbon-rich vapor mixture inlet connection 136 and a recycle vapor outlet connection 142. The inert gas and hydrocarbon-rich vapor mixture is conducted to the inlet connection 136 of the absorber column 126 by the conduit 94. As the inert gas and hydrocarbon-rich vapor mixture flows upwardly in the absorber column 126 and through the packed section 128 thereof, it is contacted by lean liquid absorbent from storage or other location flowing downwardly in the absorber 126 and through the packed section 128. As a result, a major portion of the hydrocarbon vapors in the inert gas and hydrocarbon vapor mixture is absorbed in the lean liquid absorbent. The lean liquid absorbent is conducted to the absorber 126 by a conduit 134 which is connected to the lean liquid absorbent inlet connection 132 and the internal spray nozzle 130. The rich liquid absorbent produced in the absorber 126 is separated from the inert gas and hydrocarbon vapor mixture therein and accumulates in the bottom accumulator section 135 of the absorber 126. The rich liquid absorbent is removed from the absorber 126 by way of the rich liquid absorbent outlet connection 139, a conduit 140 and a return pump 142. The rich liquid absorbent is conducted from the pump 142 to storage or other location by a conduit 146 connected to the discharge of the pump 142.

Thus, the additional process steps for liquefying and recovering hydrocarbons from the inert gas and hydrocarbon vapor mixture produced by a basic process of this invention described in connection with FIG. 5 are comprised of: (1) contacting the inert gas and hydrocarbon vapor mixture with a lean liquid absorbent whereby a major portion of the hydrocarbon vapor in the mixture is absorbed in the lean liquid absorbent; (2) separating the resulting rich liquid absorbent from the remaining inert gas and non-absorbed hydrocarbon vapor mixture; (3) conducting the rich liquid absorbent to a point of further processing or storage; and (4) recycling the remaining inert gas and non-absorbed hydrocarbon vapor to the inlet inert gas-hydrocarbon vapor mixture whereby the remaining inert gas and non-absorbed hydrocarbon vapor flows into the bed of adsorbent wherein hydrocarbon vapors are being adsorbed.

Figure 6:
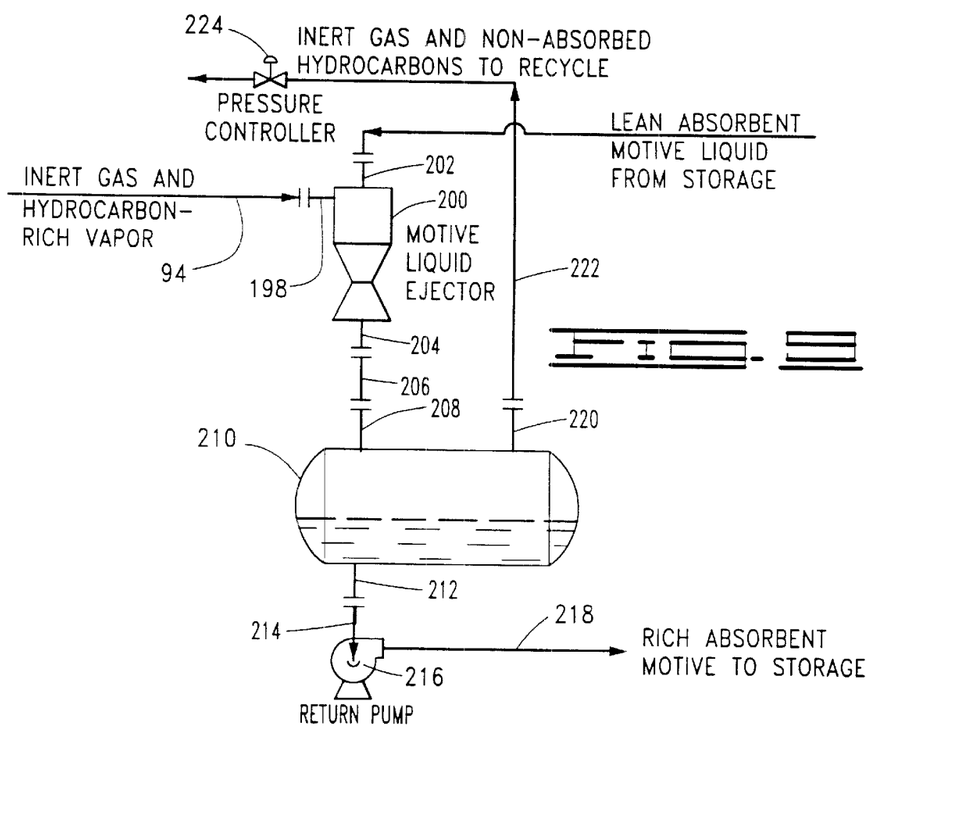
FIG. 6 is a schematic illustration of apparatus for carrying out a basic process of this invention as well as other alternate additional process steps for liquefying and recovering the hydrocarbon vapors produced by the basic process.

Referring now to FIG. 6, apparatus is illustrated for carrying out the basic process described in connection with FIG. 1 as well as other alternate additional process steps for liquefying and recovering hydrocarbon vapors from the inert gas and hydrocarbon-rich vapor mixture produced by the basic process. The apparatus of FIG. 1 is shown in FIG. 6 as is the absorber apparatus illustrated in FIG. 5, both of which include the same reference numerals as those used in FIGS. 1 and 5.

The apparatus in FIG. 6 which is in addition to that shown in FIGS. 1 and 5 includes a conduit 148 for conducting lean liquid absorbent from storage or other location to a supply pump 150. A conduit 152 is connected between the discharge of the pump 150 and the lean liquid absorbent connection 132 of the absorber column 126. A conduit 154 is connected to the conduit 152 downstream of the supply pump 150 which leads a side stream of lean liquid absorbent to the motive liquid cooler 88. A conduit 156 is connected to the motive liquid cooler 88 for removing the lean liquid absorbent therefrom and conducting it to an inlet connection 158 in the absorber 126 positioned below the packed section 128 of the absorber 126. A spray nozzle 160 disposed within the absorber column 126 is connected to the inlet connection 158. A flow control valve 162 is disposed in the conduit 152 downstream from the supply pump 150 and the connection of the conduit 154 to the conduit 152. The flow control valve 162 is used to set the desired flow rate of lean liquid absorbent to the spray nozzle 130 positioned above the packed section 128 by way of the conduit 152. A second flow control valve 163 is disposed in the conduit 154 and is used to set the flow rate of lean liquid absorbent that flows through the motive liquid cooler 88 and thereby cools the motive liquid. The resulting heated lean liquid absorbent flows from the cooler 88 through the conduit 156, the absorber inlet connection 158 and the spray nozzle 160 below the packed section 128 into the absorber 126.

Thus, the process steps for liquefying and recovering hydrocarbons from the inert gas and hydrocarbon-rich vapor mixture produced by the basic process carried out by the apparatus shown in FIG. 6 are comprised of the following steps: (1) a lean liquid absorbent from storage or other location is divided into first and second portions; (2) the first portion of the lean liquid absorbent is passed in heat exchange relationship with the motive liquid whereby the motive liquid is cooled prior to when it enters the motive liquid ejector; (3) the resulting heated first portion of the lean liquid absorbent is then utilized to contact the hydrocarbon rich inert gas-hydrocarbon vapor mixture flowing through the absorber at a point below the packed section thereof whereby a first portion of the hydrocarbon vapor in the mixture is absorbed in the first portion of the lean liquid absorbent; (4) the second portion of lean liquid absorbent is utilized to contact the inert gas-hydrocarbon rich vapor mixture flowing upwardly through the packed section of the absorber whereby a second portion of the hydrocarbon vapor in the mixture is absorbed in the second portion of the lean liquid absorbent; (5) the rich liquid absorbent flowing downwardly in the absorber is separated from the inert gas and hydrocarbon-rich vapor mixture flowing upwardly therein; (6) the rich liquid absorbent is removed from the absorber and conducted to a point of storage or other location; and (7) the remaining inert gas and non-absorbed hydrocarbon vapor and are removed from the absorber and recycled into the bed of solid absorbent wherein hydrocarbon vapors are being adsorbed.

Figure 7:
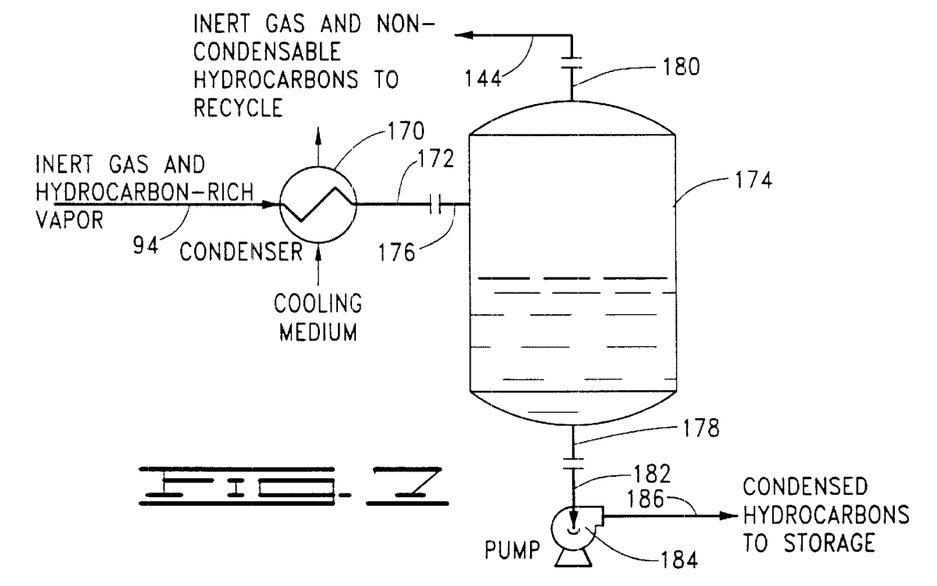
FIG. 7 is a schematic illustration of apparatus for carrying out still other additional process steps for liquefying and recovering the hydrocarbon vapor produced by a basic process.

Referring now to FIG. 7, apparatus is illustrated for carrying out still other alternate process steps that can be utilized for liquefying and recovering hydrocarbons from the inert gas and hydrocarbon-rich vapor mixture produced by the basic processes previously described and illustrated in FIGS. 1 and 2.. In accordance with the process steps, the inert gas and hydrocarbon-rich vapor mixture produced by the basic process is conducted to a non-contact condenser 170 by the conduit 94. The non-contact condenser 170 is illustrated in the form of a shell and tube heat exchanger which utilizes a cooling medium such as cooling water for condensing a majority of the hydrocarbons in the inert gas and hydrocarbon-rich vapor mixture. As will be understood, other forms of non-contact condensers using alternative coolants known in the art can also be utilized. From the condenser 170, the condensed hydrocarbons, inert gas and non-condensed hydrocarbon vapor are conducted by a conduit 172 to a separator 174. The separator 174 includes an inlet connection 176 to which the conduit 172 is attached, a hydrocarbon liquid outlet connection 178 and an inert gas and non-condensable hydrocarbon vapor outlet connection 180. The condensed hydrocarbons separated in the separator 174 are withdrawn therefrom by way of the outlet connection 178, a conduit 182 and a pump 184. The pump 184 pumps the condensed hydrocarbons to storage or other location by way of a conduit 186. The inert gas and non-condensable hydrocarbons are withdrawn from the separator by way of the outlet connection 180 and the conduit 144 which recycles the inert gas and non-condensable hydrocarbons to the adsorber in the basic process which is adsorbing hydrocarbons from the inlet inert gas-hydrocarbon vapor mixture.

Thus, the additional process steps carried out in the apparatus illustrated in FIG. 7 are comprised of: (1) the inert gas and hydrocarbon-rich vapor mixture is passed in heat exchange relationship with a cooling medium whereby a major portion of the hydrocarbon vapor in the mixture is condensed; (2) the condensed hydrocarbon vapor is separated from the remaining inert gas and non-condensable hydrocarbon mixture; (3) the separated condensed hydrocarbons are conducted to storage or a point of further processing; and (4) the remaining inert gas and non-condensable hydrocarbon vapor mixture is recycled to the bed of solid adsorbent in the basic process wherein hydrocarbon vapors are being adsorbed.

Referring now to FIG. 8, the apparatus of FIG. 7 is shown with the same reference numerals as utilized in FIG. 7 with the addition of a compressor and a back pressure controller. That is, a compressor 190 is provided connected to the conduit 94 of a basic process of this invention. The conduit 94 conducts an inert gas and hydrocarbon-rich vapor mixture to the compressor 190 wherein the mixture is compressed. A conduit 192 conducts the compressed mixture to the condenser 170 wherein a major portion of the hydrocarbons in the compressed mixture are condensed. From the condenser 170 an inert gas and non-condensed hydrocarbon vapor mixture along with condensed hydrocarbons are conducted to the inlet connection 176 of the separator 174. The condensed hydrocarbons are withdrawn from the separator 174 by way of the outlet connection 178, the conduit 182 and the pump 184. From the pump 184, the condensed hydrocarbons are conducted to storage or other location by the conduit 186. The inert gas and non-condensable hydrocarbon mixture exits the separator 174 by way of the connection 180 and is conducted by the conduit 144 to an adsorber of the basic process which is adsorbing hydrocarbons from the inlet inert gas-hydrocarbon vapor mixture. A back pressure controller 194 is disposed in the conduit 144 for maintaining a desired higher pressure in the condenser 170 and the separator 174. The higher pressure brings about the condensation of more of the hydrocarbon vapors than when the condenser and separator are operated at a lower pressure.

Referring now to FIG. 9, apparatus is illustrated for carrying out yet other additional process steps for liquefying and recovering hydrocarbons from the inert gas and hydrocarbon-rich vapor mixture produced by a basic process described in connection with FIGS. 1 or 2. The inert gas and hydrocarbon-rich vapor mixture is conducted by the conduit 94 to the inlet connection 198 of a second motive liquid ejector 200. Lean liquid absorbent motive liquid from storage or other location is conducted to the motive liquid inlet connection 202 of the ejector 200. While flowing through the ejector 200, a major portion of the hydrocarbons contained in the inert gas and hydrocarbon-rich vapor mixture are absorbed in the motive liquid. The resulting mixture of rich liquid absorbent, inert gas and non-absorbed hydrocarbon vapor is conducted to a separator 210 by way of the ejector outlet connection 204, a conduit 206 and the inlet connection 208 of the separator 210. The rich liquid absorbent separated in the separator 210 is withdrawn therefrom by way of an outlet connection 212, a conduit 214 and a return pump 216. The return pump 216 pumps the rich liquid absorbent by way of a conduit 218 to storage or other location. The inert gas and non-absorbed hydrocarbon vapor are withdrawn from the separator 210 by way of an outlet connection 220 and a conduit 222. The conduit 222 includes a back pressure controller disposed therein for maintaining a desired higher pressure in the separator 210 than that produced by the ejector 200 to bring about the condensation of more of the hydrocarbon vapors than when the separator is operated at a lower pressure. The conduit 222 recycles the inert gas and non-absorbed hydrocarbon vapor to the adsorber of the basic process which is adsorbing hydrocarbons from the inlet inert gas-hydrocarbon vapor mixture.

Thus, the additional process steps that can be utilized with a basic process of this invention carried out in the apparatus illustrated in FIG. 9 include the steps of: (1) conducting the inert gas and hydrocarbon-rich vapor mixture produced by the basic process to a second motive liquid ejector operated by a motive liquid having an infinity for hydrocarbon vapor whereby a major portion of the hydrocarbon vapor is absorbed in the motive liquid; (2) separating the motive liquid having the hydrocarbon vapor absorbed therein from the remaining inert gas and non-absorbed hydrocarbon vapor mixture; (3) conducting the motive liquid having hydrocarbon vapor absorbed therein to storage or other location; and (4) recycling the remaining inert gas and non-absorbed hydrocarbon vapor to the adsorber of the basic process which is adsorbing the inlet inert gas-hydrocarbon vapor mixture.

Operation of the Apparatus 10

In operation of the apparatus 10 illustrated in FIGS. 1 and 2 for carrying out the basic processes of this invention, the switching valves 32, 34, 38, 40, 50 and 52 are operated in a manner whereby the inlet inert gas-hydrocarbon vapor mixture is caused to flow through one of the absorbers 12 or 14 while the other of the absorbers is being regenerated. For example, during a first cycle, the switching valve 32 is open and the switching valve 34 closed whereby the inlet inert gas-hydrocarbon vapor mixture flows into the adsorber 12 by way of the conduit 28, switching valve 32 and connection 16 of the adsorber 12. Because the switching valve 34 disposed in the conduit 30 is closed, the inlet inert gas-hydrocarbon vapor mixture is prevented from entering the adsorber 14. The switching valve 50 disposed in the conduit 46 is open and the switching valve 52 disposed in the conduit 48 is closed whereby the residue gas stream produced in the adsorber 12 exits the adsorber 12 by way of the connection 18 thereof, the conduit 46 and the switching valve 50 and enters the header 44. From the header 44, the residue gas stream flows through the conduit 54 from where it is vented to the atmosphere. The switching valve 38 disposed in the header 36 is closed and the switching valve 40 disposed therein is open whereby the adsorbent bed within the adsorber 14 is communicated by way of the conduit 42 with the ejector 72. The switching valve 60 in the conduit 56 is closed and the switching valve 66 in the conduit 62 is initially closed.

During the first part of the cycle when the switching valves are in the mode described above, the inlet inert gas hydrocarbon vapor mixture flows through the bed of adsorbent within the adsorber 12 whereby hydrocarbons are adsorbed on the bed and removed from the mixture. The residue gas produced which is comprised of substantially hydrocarbon-free inert gas is vented to the atmosphere by way of the inert gas vent 54. Simultaneously, the bed of adsorbent disposed within the adsorber 14 is evacuated by the motive liquid ejector 72 whereby hydrocarbons are desorbed therefrom. An inert gas and hydrocarbon-rich vapor mixture is withdrawn from the adsorbent bed within the adsorber 14 by the motive liquid ejector 72 and the inert gas and hydrocarbon-rich vapor mixture commingled with motive liquid are discharged from the ejector into the separator 82. The separated inert gas and hydrocarbon-rich vapor mixture is withdrawn from the separator by way of the conduit 94 and the separated motive liquid is recycled to the ejector 72 by way of the conduit 86, the motive liquid cooler 88 and the motive liquid pump 90 (FIG. 1), or the separated motive liquid is returned to storage or to a separate process by way of the conduit 96, the pump 92 and the optional cooler 94 (FIG. 2). During the last part of the cycle, after a major portion of hydrocarbons adsorbed on the bed of adsorbent within the adsorber 14 have been desorbed therefrom by the operation of the motive liquid ejector 72, the switching valve 66 in the conduit 62 is opened whereby a quantity of hydrocarbon-free stripping inert gas flows by way of the conduit 62, the switching valve 66 and the connection 64 of the adsorber 14 into the adsorber 14. The stripping inert gas flows through the bed of adsorbent contained in the adsorber 14 and is withdrawn therefrom by the motive liquid ejector 72 as previously described. The introduction of a quantity of stripping inert gas into the adsorbent bed contained within the adsorber 14 functions to strip additional hydrocarbons from the bed which were not desorbed therefrom by the operation of the motive liquid ejector 72, i.e., by the lowering of the pressure exerted on the bed to the degree of vacuum achieved by the ejector 72.

After the adsorbent bed within the adsorber 14 has been fully regenerated and the adsorbent bed within the adsorber 12 loaded with hydrocarbons from the inert gas-hydrocarbon vapor mixture flowing therethrough, the switching valves are reversed. That is, the switching valves 32 and 50 are closed, the switching valves 34 and 52 are opened, the switching valve 38 is open and the switching 40 is closed. This causes the flow pattern of the inlet inert gas-hydrocarbon vapor mixture to be changed whereby the mixture flows through the regenerated adsorbent bed within the adsorber 14 and the residue gas therefrom to be vented to the atmosphere. The adsorbent bed within the adsorber 12 is simultaneously communicated with the motive liquid ejector 72 whereby the bed is evacuated and the switching valve 60 is open during a latter part of the cycle as described above to strip the adsorbent bed whereby additional hydrocarbons are desorbed therefrom. As is well understood by those skilled in the art, the flow pattern of the inlet inert gas-hydrocarbon vapor mixture and the bed being regenerated are continuously changed or cycled whereby when the adsorbent bed through which the inlet vapor mixture is flowing becomes loaded with adsorbed hydrocarbons, the inlet mixture is caused to flow into the bed which has just been regenerated and the bed which is loaded with adsorbed hydrocarbons is regenerated. The inert gas and hydrocarbon-rich vapor mixture produced from the bed being regenerated is separated from the motive liquid and is disposed of or subjected to additional process steps as described above for liquefying and recovering hydrocarbons from the inert gas and hydrocarbon-rich vapor mixture.

The operation of the apparatus 10 illustrated in FIG. 3 is essentially the same as the operation described above for the apparatus shown in FIGS. 1 and 2 except that the motive liquid also functions as an absorbent for the evacuated hydrocarbon vapors, and the inert gas and non-absorbed hydrocarbon vapor separated from the hydrocarbon rich absorbent are recycled to the adsorber in which hydrocarbons are being adsorbed. The lean absorbent motive liquid utilized is passed through the ejector 72 only once.

The operation of the various additional process steps for liquefying and recovering hydrocarbons from the inert gas and hydrocarbon-rich vapor mixture produced by the basic processes carried out in the apparatus of FIGS. 1 and 2 will be readily understood by those skilled in the art from a reading of the descriptions of such processes given above.

The hydrocarbon vapor recovery processes described herein which utilize a motive liquid ejector in lieu of one or more vacuum pumps are considerably less expensive and less complex as well as being easier and less expensive to install and operate.

Thus, the present invention is well adapted to carry out the objects and attain the ends and advantages mentioned as well as those which are inherent therein. While presently preferred embodiments of the invention have been described for purposes of this disclosure, numerous changes in the arrangement of process steps and apparatus elements will suggest themselves to those skilled in the art, which changes are encompassed within the spirit of this invention as defined by the appended claims.

What is claimed is:

1. An improved process for recovering hydrocarbon vapors from an inlet inert gas-hydrocarbon vapor mixture comprising the steps of:

(a) flowing said inlet mixture through a first bed of solid adsorbent having an affinity for hydrocarbon vapors whereby hydrocarbon vapors are adsorbed on said bed and a residue gas stream comprised of substantially hydrocarbon-free inert gas is produced;

(b) venting said substantially hydrocarbon-free inert gas to the atmosphere;

(c) evacuating a second bed of solid adsorbent having hydrocarbon vapors adsorbed thereon with an ejector operated by a motive liquid whereby a major portion of said hydrocarbon vapors is desorbed from said bed and an inert gas and hydrocarbon-rich vapor mixture commingled with said motive liquid is produced;

(d) separating said inert gas and hydrocarbon-rich vapor mixture from said motive liquid;

(e) conducting said inert gas and hydrocarbon rich vapor mixture to a point of additional processing or disposal; and (f) periodically changing the flow pattern of said inlet inert gas-hydrocarbon vapor mixture and changing the bed of solid adsorbent being evacuated whereby when the bed through which the inlet inert gas-hydrocarbon vapor mixture is flowing becomes loaded with adsorbed hydrocarbon vapors, the inlet inert gas-hydrocarbon vapor mixture is caused to flow through the bed which has just been evacuated and the bed loaded with adsorbed hydrocarbon vapors is caused to be regenerated.

2. The process of claim 1 wherein said inert gas is selected from the group consisting of air, nitrogen and carbon dioxide.

3. The process of claim 1 wherein said hydrocarbon vapor is selected from the group consisting of gasoline vapors, distillate vapors, benzene vapor, chlorinated and other hydrocarbon solvent vapors and alcohol vapors.

4. The process of claim 1 wherein said motive liquid is selected from the group consisting of glycol, water, petroleum based oils, hydrocarbon liquids, alcohols and various synthetic fluids.

5. The process of claim 1 which further comprises the step of introducing a quantity of hydrocarbon-free inert gas into said second bed while evacuating said second bed in accordance with step (c) whereby additional hydrocarbons are stripped from said second bed.

6. The process of claim 1 wherein said motive liquid separated in accordance with step (d) is recirculated to said ejector.

7. The process of claim 6 wherein said motive liquid is cooled prior to being recirculated to said ejector.

8. An improved process for recovering hydrocarbon vapors from an inlet inert gas-hydrocarbon vapor mixture comprising the steps of:

(a) flowing said inlet mixture through a first bed of solid adsorbent having an affinity for hydrocarbon vapors whereby hydrocarbon vapors are adsorbed on said bed and a residue gas stream comprised of substantially hydrocarbon-free inert gas is produced;

(b) venting said substantially hydrocarbon-free inert gas to the atmosphere;

(c) evacuating a second bed of solid adsorbent having hydrocarbon vapors adsorbed thereon with an ejector operated by a lean absorbent motive liquid from a separate process or storage having an affinity for said hydrocarbon vapors whereby a major portion of said hydrocarbon vapors is desorbed from said bed and a major portion of said desorbed hydrocarbon vapors is absorbed in said motive liquid thereby forming a hydrocarbon-rich absorbent motive liquid and an inert gas-non-absorbed hydrocarbon vapor mixture commingled with said hydrocarbon-rich motive liquid;

(d) separating said inert gas-non-absorbed hydrocarbon vapor mixture from said hydrocarbon-rich absorbent motive liquid;

(e) recycling said separated inert gas-non-absorbed hydrocarbon vapor mixture to said inlet inert gas-hydrocarbon vapor mixture prior to when said inlet mixture flows through said first bed of solid adsorbent wherein hydrocarbon vapors are being adsorbed in accordance with step (a); and (f) periodically changing the flow pattern of said inlet inert gas-hydrocarbon vapor mixture and changing the bed of solid adsorbent being evacuated whereby when the bed through which the inlet inert gas-hydrocarbon vapor mixture is flowing becomes loaded with adsorbed hydrocarbon vapors, the inlet inert gas-hydrocarbon vapor mixture is caused to flow through the bed which has just been evacuated and the bed loaded with adsorbed hydrocarbon vapors is caused to be regenerated.

9. The process of claim 8 which further comprises the step of introducing a quantity of hydrocarbon-free inert gas into said second bed while evacuating said second bed in accordance with step (c) whereby additional hydrocarbon vapors are stripped from said second bed.

10. The process of claim 9 wherein said hydrocarbon-rich absorbent motive liquid separated in accordance with step (d) is returned to said separate process or storage.

11. The process of claim 1 which further comprises the additional process steps of:

(g) contacting said inert gas and hydrocarbon-rich vapor mixture separated in accordance with step (d) with a lean liquid absorbent whereby a major portion of said hydrocarbon vapors in said mixture are absorbed in said lean liquid absorbent;

(h) separating the resulting rich liquid absorbent from the remaining inert gas and non-absorbed hydrocarbon vapors;

(i) conducting said rich liquid absorbent to a point of further processing or storage; and (j) recycling the remaining inert gas and non-absorbed hydrocarbon vapors separated in step (h) to said inlet inert gas-hydrocarbon vapor mixture prior to when said inlet mixture flows through said bed of solid adsorbent wherein hydrocarbon vapors are being adsorbed in accordance with step (a).

12. The process of claim 1 which further comprises the additional process steps of:

(g) contacting said inert gas and hydrocarbon-rich vapor mixture separated in accordance with step (d) with condensed hydrocarbon liquid whereby a major portion of said hydrocarbon vapors in said mixture are also condensed;

(h) separating the condensed hydrocarbon liquid produced in step (g) from the remaining inert gas non-condensed hydrocarbon vapors;

(i) recycling a portion of said condensed hydrocarbon liquid separated in step (h) into contact with said inert gas and hydrocarbon-rich vapor mixture in accordance with step (a);

(j) conducting the remaining condensed hydrocarbon liquid separated in step (h) to a point of further processing or storage;

(k) recycling the remaining inert gas and non-condensed hydrocarbon vapors separated in step (h) to said inlet inert gas-hydrocarbon vapor mixture prior to when said inlet mixture flows through said bed of solid adsorbent wherein hydrocarbon vapors are being adsorbed in accordance with step (a).

13. The process of claim 6 which further comprises the additional process steps of:

(g) dividing a lean liquid absorbent into first and second portions;

(h) passing said first portion of said lean liquid absorbent in heat exchange relationship with said motive liquid whereby said motive liquid is cooled prior to step (c);

(i) contacting said inert gas and hydrocarbon-rich vapor mixture separated in accordance with step (d) with said first portion of said lean liquid absorbent in an absorber whereby a portion of said hydrocarbon vapors in said mixture is absorbed in said lean liquid absorbent;

(j) contacting the remaining inert gas and hydrocarbon-rich vapor mixture separated in accordance with step (d) with said second portion of lean liquid absorbent in said absorber whereby a second portion of said hydrocarbon vapors in said mixture is absorbed in said second portion of lean liquid absorbent;

(k) separating the resulting combined rich liquid absorbent from the remaining inert gas and non-absorbed hydrocarbon vapors;

(l) conducting the resulting combined rich liquid absorbent from said absorber to a point of further processing or storage; and (m) recycling the remaining inert gas and non-absorbed hydrocarbon vapors separated in step (k) to said inlet inert gas-hydrocarbon vapor mixture prior to when said inlet mixture flows through said bed of solid adsorbent wherein hydrocarbon vapors are being adsorbed in accordance with step (a).

14. The process of claim 1 which further comprises the additional process steps of:

(g) passing said inert gas and hydrocarbon-rich vapor mixture in heat exchange relationship with a cooling medium whereby a major portion of said hydrocarbon vapors in said mixture are condensed;

(h) separating said condensed hydrocarbon vapors from the remaining inert gas and non-condensed hydrocarbon vapor mixture;

(i) conducting the separated condensed hydrocarbon vapors to a point of further processing or storage; and (j) recycling said remaining inert gas and non-condensed hydrocarbon vapor mixture separated in step (h) to said inlet inert gas-hydrocarbon vapor mixture prior to when said inlet mixture flows through said bed of solid adsorbent wherein hydrocarbon vapors are being adsorbed in accordance with step (a).

15. The process of claim 14 which further comprises the step of compressing said inert gas and hydrocarbon-rich vapor mixture prior to step (g).

16. The process of claim 1 which further comprises the additional process steps of:

(g) conducting said inert gas and hydrocarbon-rich vapor mixture separated in accordance with step (d) to a second ejector operated by a motive liquid having an affinity for hydrocarbon vapors whereby a major portion of said hydrocarbon-rich vapors is absorbed in said motive liquid;

(h) separating said motive liquid having said hydrocarbon vapors absorbed therein from the remaining inert gas and non-absorbed hydrocarbon vapor mixture;

(i) conducting said motive liquid having said hydrocarbon vapors absorbed therein to a point of further processing or storage; and recycling the remaining inert gas and non-absorbed hydrocarbon vapor mixture separated in step (h) to said inlet inert gas-hydrocarbon vapor mixture prior to when said inlet mixture flows through said bed of solid adsorbent wherein hydrocarbon vapors are being adsorbed in accordance with step (a).

17. An improved process for recovering hydrocarbon vapors from an inlet inert gas-hydrocarbon vapor mixture comprising the steps of:

(a) flowing said inlet mixture through a first bed of solid adsorbent having an affinity for hydrocarbon vapors whereby hydrocarbon vapors are adsorbed on said bed and a residue gas stream comprised of substantially hydrocarbon-free inert gas is produced;

(b) venting said substantially hydrocarbon-free inert gas to the atmosphere;

(c) evacuating a second bed of solid adsorbent having hydrocarbon vapors adsorbed thereon with an ejector operated by a motive liquid whereby a major portion of said hydrocarbon vapors is desorbed from said bed and an inert gas and hydrocarbon-rich vapor mixture commingled with said motive liquid is produced;

(d) separating said inert gas and hydrocarbon-rich vapor mixture from said motive liquid;

(e) periodically changing the flow pattern of said inlet inert gas-hydrocarbon vapor mixture and changing the bed of solid adsorbent being evacuated whereby when the bed through which the inlet inert gas-hydrocarbon vapor mixture is flowing becomes loaded with adsorbed hydrocarbon vapors, the inlet inert gas-hydrocarbon vapor mixture is caused to flow through the bed which has just been evacuated and the bed loaded with adsorbed hydrocarbon vapors is caused to be regenerated;

(f) contacting said inert gas and hydrocarbon-rich vapor mixture separated in accordance with step (d) with a lean liquid absorbent whereby a major portion of said hydrocarbon vapors in said mixture is absorbed in said lean liquid absorbent;

(g) separating the resulting rich liquid absorbent from the remaining inert gas and non-absorbed hydrocarbon vapors;

(h) conducting said rich liquid absorbent to a point of further processing or storage; and (i) recycling the remaining inert gas and non-absorbed hydrocarbon vapors separated in step (g) to said inlet inert gas-hydrocarbon vapor mixture prior to when said inlet mixture flows through said bed of solid adsorbent wherein hydrocarbon vapors are being adsorbed in accordance with step (a).

18. The process of claim 17 wherein said inert gas is selected from the group consisting of air, nitrogen and carbon dioxide.

19. The process of claim 17 wherein said hydrocarbon vapor is selected from the group consisting of gasoline vapors, distillate vapors, benzene vapor, chlorinated and other hydrocarbon solvent vapors and alcohol vapors.

20. The process of claim 17 wherein said motive liquid is selected from the group consisting of glycol, water, petroleum based oils, hydrocarbon liquids, alcohols and various synthetic fluids.

21. The process of claim 17 which further comprises the step of introducing a quantity of hydrocarbon-free inert gas into said second bed while evacuating said second bed in accordance with step (c) whereby additional hydrocarbon vapors are stripped from said second bed.

22. The process of claim 17 wherein said motive liquid is recirculated to said ejector.

23. The process of claim 17 wherein said motive liquid is cooled prior to being recirculated to said ejector.

24. The process of claim 17 wherein said motive liquid is a continuous stream which passes through said ejector only once.

25. An improved process for recovering hydrocarbon vapors from an inlet inert gas-hydrocarbon vapor mixture comprising the steps of:

(a) flowing said inlet mixture through a first bed of solid adsorbent having an affinity for hydrocarbon vapors whereby hydrocarbon vapors are adsorbed on said bed and a residue gas stream comprised of substantially hydrocarbon-free inert gas is produced;

(b) venting said substantially hydrocarbon-free inert gas to the atmosphere;

(c) evacuating a second bed of solid adsorbent having hydrocarbon vapors adsorbed thereon with an ejector operated by a lean absorbent motive liquid from a separate process or storage having an affinity for said hydrocarbon vapors whereby a major portion of said adsorbed hydrocarbon vapors is desorbed from said bed and a major portion of said desorbed hydrocarbon vapors is absorbed in said motive liquid thereby forming a hydrocarbon-rich absorbent motive liquid and an inert gas-non-absorbed hydrocarbon vapor mixture commingled with said hydrocarbon-rich motive liquid;

(d) separating said hydrocarbon rich motive liquid from said inert gas-non-absorbed hydrocarbon vapor mixture;

(e) conducting said hydrocarbon rich motive liquid to said separate process or storage;

(f) recycling said separated inert gas-non-absorbed hydrocarbon vapor mixture to said inlet inert gas-hydrocarbon vapor mixture prior to when said inlet mixture flows through said bed of solid adsorbent wherein hydrocarbon vapors are being adsorbed in accordance with step (a); and (g) periodically changing the flow pattern of said inlet inert gas-hydrocarbon vapor mixture and changing the bed of solid adsorbent being evacuated whereby the bed through which the inlet inert gas-hydrocarbon vapor mixture is flowing becomes loaded with adsorbed hydrocarbon vapors, the inlet inert gas-hydrocarbon vapor mixture is caused to flow through the bed which has just been evacuated and the bed loaded with adsorbed hydrocarbon vapors is caused to be regenerated.

26. The process of claim 25 wherein said inert gas is selected from the group consisting of air, nitrogen and carbon dioxide.

27. The process of claim 25 wherein said hydrocarbon vapors are selected from the group consisting of gasoline vapors, distillate vapors, benzene vapor, chlorinated and other hydrocarbon solvent vapors and alcohol vapors.

28. The process of claim 25 wherein said motive liquid is selected from the group consisting of glycol, water, petroleum based oils, hydrocarbon liquids, alcohols and various synthetic fluids.

29. The process of claim 25 which further comprises the step of introducing a quantity of hydrocarbon-free inert gas into said second bed while evacuating said second bed in accordance with step (c) whereby additional hydrocarbon vapors are stripped from said second bed.

30. The process of claim 25 wherein said hydrocarbon-rich motive liquid is cooled prior to step (e).

* * * * *